United States Patent
Lee

(10) Patent No.: US 7,738,090 B1
(45) Date of Patent: Jun. 15, 2010

(54) FOURIER FILTERS, SYSTEMS FOR FABRICATING FOURIER FILTERS, AND SYSTEMS AND METHODS FOR INSPECTING A SPECIMEN USING FOURIER FILTERS

(75) Inventor: Shing Lee, Fremont, CA (US)

(73) Assignee: KLA-Tencor Corporation, San Jose, CA (US)

( * ) Notice: Subject to any disclaimer, the term of this patent is extended or adjusted under 35 U.S.C. 154(b) by 445 days.

(21) Appl. No.: 11/754,485

(22) Filed: May 29, 2007

(51) Int. Cl.
*G01N 21/00* (2006.01)

(52) U.S. Cl. .................................... 356/237.2

(58) Field of Classification Search ........................ None
See application file for complete search history.

(56) References Cited

U.S. PATENT DOCUMENTS

| | | | |
|---|---|---|---|
| RE33,956 E | 6/1992 | Lin et al. | |
| 5,177,559 A | 1/1993 | Batchelder et al. | |
| 5,428,442 A | 6/1995 | Lin et al. | |
| 5,576,829 A | 11/1996 | Shiraishi et al. | |
| 5,970,168 A | 10/1999 | Montesanto et al. | |
| 6,603,541 B2 | 8/2003 | Lange | |
| 6,791,680 B1 * | 9/2004 | Rosengaus et al. | 356/237.2 |
| 7,180,084 B2 | 2/2007 | Weiss et al. | |

OTHER PUBLICATIONS

U.S. Appl. No. 11/464,567 entitled "Systems Configured to Inspect a Specimen," filed Aug. 15, 2006.
U.S. Appl. No. 11/683,554 entitled "Fourier Filters, Inspection Systems, and Systems for Fabricating Fourier Filters," filed Mar. 8, 2007.

* cited by examiner

*Primary Examiner*—Tu T Nguyen
(74) *Attorney, Agent, or Firm*—Kevin L. Daffer; Daffer McDaniel, LLP

(57) ABSTRACT

Fourier filters, systems configured to fabricate Fourier filters and systems and methods configured to inspect specimens are provided herein. One Fourier filter configured for use in an inspection system comprises an array of patterned features formed within an optically opaque layer. The array of patterned features is generally configured to block light reflected and diffracted from structures on a specimen and to allow light scattered from defects on the specimen to pass through the filter. The array of patterned features is generally formed by removing select portions of the optically opaque layer to create transmissive regions, which only allow the light scattered from the defects to pass through. In one embodiment, the select portions of the optically opaque layer are removed with laser light.

30 Claims, 5 Drawing Sheets

FOURIER FILTERS, SYSTEMS FOR FABRICATING FOURIER FILTERS, AND SYSTEMS AND METHODS FOR INSPECTING A SPECIMEN USING FOURIER FILTERS

BACKGROUND OF THE INVENTION

1. Field of the Invention

This invention relates to Fourier filters, systems for fabricating Fourier filters and systems and methods for inspecting a specimen using Fourier filters. Certain embodiments relate to a Fourier filter that includes an array of patterned features formed within an optically opaque layer. A dry process is used to form the array of patterned features by removing select portions of the optically opaque layer to create transmissive regions, which only allow light scattered from the defects to pass through the Fourier filter. Light reflected and diffracted from periodic structures on the specimen is substantially blocked by the array of patterned features.

2. Description of the Related Art

The following descriptions and examples are given as background only.

Fabricating semiconductor devices such as logic and memory devices typically includes processing a substrate using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Many different types of inspection tools have been developed for the inspection of semiconductor wafers. Defect inspection is currently performed using techniques such as bright field (BF) imaging, dark field (DF) imaging, and scattering. The type of inspection tool that is used for inspecting semiconductor wafers may be based on, for example, characteristics of the defects of interest and characteristics of the wafers that will be inspected. For example, some inspection tools are designed to inspect unpatterned semiconductor wafers, while others are designed to inspect patterned semiconductor wafers.

Inspection tools for unpatterned wafers are generally not capable of inspecting patterned wafers for a number of reasons. For example, many unpatterned wafer inspection tools are configured such that all of the light collected by a lens or another collector is directed to a single detector. The detector generates a single output signal representative of all of the collected light. Therefore, light scattered from patterned features on the specimen will be combined with other scattered light. This prohibits the other scattered light (e.g., light scattered from defects or other surface irregularities) from being detected separately from the light scattered from the patterned features.

Patterned wafer inspection is of particular interest and importance to the semiconductor industry because processed semiconductor wafers usually have a pattern of features formed thereon. In some cases, unpatterned wafers, or "monitor wafers," which have been run through a process tool, may be inspected as a gauge for the number and types of defects that may be found on patterned wafers, or "product wafers." However, the defects detected on monitor wafers do not always accurately reflect the defects that are detected on product wafers after the same process in the same process tool. Inspection of product wafers is, therefore, important to accurately detect defects that may have been formed on the wafer during, or as a result of, processing. In other words, inspecting product wafers may provide more accurate monitoring and control of processes and process tools than inspection of monitor wafers.

Many inspection tools have been developed for patterned wafer inspection. Some patterned wafer inspection tools utilize spatial filters to separate light scattered from patterned features from other scattered light, so that the other scattered light may be separately detected. Since the light scattered from patterned features depends on various characteristics of the patterned features (e.g., lateral dimension and period), the design of the spatial filter also depends on the characteristics of the patterned features. As a result, the spatial filter must be designed based on known or determined characteristics of the patterned features and must vary as different patterned features are inspected.

A Fourier filter is one type of spatial filter that may be used as described above. Fourier filters are relatively useful for filtering light from repetitive patterns, such as memory arrays formed on a wafer, so that defects or other surface irregularities may be more easily detected. Various methods have been used in the past to provide Fourier filtering.

One method of Fourier filtering is the mechanical method. This method utilizes mechanical rods (or other mechanical devices) to block the diffraction pattern generated by array structures, so that the energy from the array is removed from the optical path of the inspection system. Although the mechanical method is widely used, it has a number of disadvantages, particularly for flood illumination based inspection systems.

Flood illumination based inspection systems produce diffraction peaks that show up as "dots" in the image plane. The rods used in the mechanical method block excessive amounts of light in these systems, thereby reducing the overall defect signal. In addition, the mechanical method induces significantly more Fourier filter ringing, which reduces defect sensitivity. For example, Fourier filters in the form of periodic blocking bars diffract light into undesirable directions, inducing "ringing" or side lobes in the defect signals. In some cases, the side lobes may produce significant distortion at the image plane of the inspection system, adversely affecting the ability of the inspection system to detect defects on the wafer with high accuracy. Furthermore, the rods must have a relatively large diameter in order to be structurally sound. As such, only a limited number of rods can be used; otherwise, the entire plane would be blocked by the rods.

Another method for Fourier filtering is the liquid crystal method. This method utilizes a one- or two-dimensional liquid crystal device to block the diffraction pattern generated by array structures, so that the energy from the array is removed from the optical path of the inspection system. Currently used liquid crystal Fourier filter devices are programmable and capable of filtering out diffraction dots in a two-dimensional manner. However, there are several factors that make liquid crystal devices inappropriate for flood illumination based inspection systems. For example, the use of a liquid crystal device as a Fourier filter utilizes the principle of light scattering. However, light scattering significantly alters the wavefront of the inspection system, causing severe degradation to the image quality. In addition, most liquid crystal material has a damage threshold at a wavelength of approximately 300 nm, making liquid crystal devices less than ideal for use in deep ultraviolet (DUV) based systems (i.e., systems that operate at wavelength(s) less than about 300 nm).

Chrome masks have also been used for Fourier filtering. Chrome mask Fourier filters are generally fabricated with optical or electron beam lithography processes to include opaque chrome regions arranged in a pattern on a substantially transparent substrate. Masks fabricated with such processes tend to provide good repeatability and matching and have been used to make ICs for many years. For example, a chrome mask may be fabricated by depositing chrome on the substrate, patterning the chrome by lithography and etch, and cleaning the substrate with the patterned chrome formed thereon. As such, a chrome mask Fourier filter may be tailored or "programmed" to block the diffraction pattern produced by a particular array of structures.

However, chrome masks are not used in many inspection systems due to the relatively long turn around time and relatively high cost associated with fabricating such filters. For example, most semiconductor fabrication facilities do not have dedicated lithography and cleaning stations for Fourier filter fabrication. As such, chrome mask designs are often sent out to a mask shop for fabrication. However, sending filter designs out for fabrication often results in several days of down time for the inspection system. This makes chrome mask Fourier filters unsuitable for situations in which a fast turn around time is beneficial (such as during process development).

Accordingly, a need exists for an improved Fourier filter, which overcomes the disadvantages described above. In particular, a need exists for a two-dimensional, programmable Fourier filter suitable for flood illuminated dark field wafer inspection systems, which: (i) does not block excessive amounts of light, (ii) does not induce significant Fourier filter ringing or periphery energy leakage, (iii) does not significantly alter the wavefront of the inspection system, (iv) does not cause degradation of the image, and (v) does not suffer from long turn around time or high cost. The Fourier filter should also be structurally sound and suitable for use at DUV and other wavelengths.

SUMMARY OF THE INVENTION

The following description of various embodiments of Fourier filters, systems for fabricating Fourier filters, and systems and methods for inspecting a specimen is not to be construed in any way as limiting the subject matter of the appended claims.

According to one embodiment, a Fourier filter is provided herein for use in an inspection system. In general, the Fourier filter may include an array of patterned features formed within an optically opaque layer. The array of patterned features may be configured to block light reflected and diffracted from structures on a specimen and to allow light scattered from defects on the specimen to pass through the filter. In some embodiments, the array of patterned features may include a two-dimensional (2D) array of the patterned features. However, the array of patterned features is not limited to 2D arrays and may include a 1D array of patterned features in at least one embodiment of the invention.

In most cases, a dry process may be used to form the array of patterned features by removing select portions of the optically opaque layer to create transmissive regions, which only allow the light scattered from defects on the specimen to pass through. In some embodiments, for example, the transmission regions may be created by removing the select portions of the optically opaque layer with laser light. However, the means for removal is not limited to dry processes or laser light in all embodiments of the invention. For example, a wet process (such as a water jet) may be used for removing the select portions in at least one embodiment of the invention.

In general, the select portions of the optically opaque layer may be removed, such that each of the patterned features in the array includes an optically opaque center portion surrounded by at least one transmissive region. In some embodiments, a shape of the optically opaque center portion may be substantially circular. However, the optically opaque center portion is not limited to a circular shape in all embodiments of the invention. In other embodiments, the shape of the optically opaque center portion may be substantially different from circular depending on the optical aberrations, flare and ghosting of the system, as well as the surface roughness the sample. In particular, the Fourier filter design may be based on images obtained from the Fourier plane. Regardless of the particular filter design, the optically opaque center portion may be formed with rough edges, in some embodiments of the invention, to reduce any ringing that may be induced by the Fourier filter.

In general, the optically opaque layer may include a number of different materials. In one embodiment, the optically opaque layer may include a relatively thin layer of metal formed upon an optically transmissive substrate. In one example, the optically transmissive substrate may include a material selected from a group comprising fused silica, calcium fluoride and magnesium fluoride. The optically transmissive substrate may be coated with an antireflective (AR) coating before the relatively thin layer of metal is formed thereon to reduce back reflection, optical flare and ghosting. In one example, the relatively thin layer of metal may include a material, such as gold, chromium and aluminum, although other suitable metal materials may be used. In such an embodiment, laser light may be used to evaporate select portions of the relatively thin layer of metal, while leaving the optically transmissive substrate in tact with the pattern of features formed thereon.

In another embodiment, the optically opaque layer may include a relatively thin sheet of metal or plastic. In one example, the relatively thin sheet of metal may be selected from a group comprising stainless steel, aluminum and nickel. However, substantially any metal sheet capable of effectively blocking DUV light with a skin depth of less than a few microns can also be used. Although stainless steel may be preferred in some embodiments for its mechanical integrity, other metallic materials may also be good candidates. In one example, the relatively thin sheet of plastic may be selected from a group comprising polycarbonate, acrylic and PEEK substrates. In some cases, the relatively thin sheet of plastic may be coated with a metallic material to prevent the plastic from outgassing when exposed to ultraviolet (UV) light. For example, a plasma assisted sputter coating procedure may be used to coat the relatively thin sheet of plastic in some embodiments.

When a relatively thin sheet of metal or plastic is used, the optically opaque center portion may be surrounded by two or more transmissive regions and suspended there between by two or more thin strips (i.e., "spider legs") of the optically opaque layer. However, the spider legs may comprise a relatively small width (e.g., on the order of tens microns), and thus, may not substantially block the pupil plane. In some embodiments, laser light may be used to cut out portions of the optically opaque layer, leaving the optically opaque center portion and thin strips in tact. However, alternative means (e.g., a water jet) may be used for removing the select portions and thereby creating the transmissive regions in at least one embodiment of the invention.

According to another embodiment, a system is provided herein for inspecting a specimen. In general, the system may include an illumination subsystem configured to illuminate a two-dimensional field of view (FOV) on the specimen, a collection subsystem configured to collect light from the specimen, and a detection subsystem configured to generate output that can be used for detecting defects on the specimen. In one embodiment, the system may be configured as a flood illuminated dark field (DF) inspection system. However, the system may be alternatively configured in at least one embodiment of the invention.

The system may also include a Fourier filter positioned at a Fourier plane of the collection subsystem. As noted above, the Fourier filter may include an array of patterned features formed within an optically opaque layer. The array of patterned features may be configured to block light reflected and diffracted from structures on the specimen and to allow light scattered from defects on the specimen to pass through the filter to the detection subsystem of the system. The array of patterned features may be formed as described further herein. For example, the array of patterned features may be formed by removing portions of the optically opaque layer to create transmissive regions, which only allow the light scattered from the defects to pass through. Positioning the Fourier filter within the Fourier plane of the inspection system enables the detection subsystem to generate output responsive to light passed through the transmissive regions, so that the output can be used for detecting the defects on the specimen.

According to a further embodiment, a system is provided herein for fabricating a Fourier filter for use in an inspection system. In general, the system may include an optical subsystem, a fabrication subsystem and a control subsystem. The optical subsystem may be configured to generate an image of light in a Fourier plane of the inspection system, where the image comprises light reflected and diffracted from structures on a specimen. The fabrication subsystem may be configured to fabricate the Fourier filter by using laser light (in at least one embodiment of the invention) to form an array of patterned features within an optically opaque layer. The control subsystem may control the fabrication subsystem based on the image generated by the optical subsystem, so that the array of patterned features is formed to block substantially all of the light reflected and diffracted from the structures on the specimen. In some embodiments, the control subsystem may further control the fabrication subsystem, such that the patterned features are formed with rough edges.

In some embodiments, the fabrication subsystem may generally include a holder and a laser. The holder may be configured to align the optically opaque layer within the fabrication subsystem. The laser may be configured to form the array of patterned features by removing select portions of the optically opaque layer under control of the control subsystem. As noted above, the select portions removed by the laser may only allow light scattered from defects on the specimen to pass through the Fourier filter. As such, the Fourier filter formed by the fabrication subsystem may enable defects to be detected more easily.

In general, the laser may include any appropriate laser source (e.g., a semiconductor, fiber or $CO_2$ laser source) having any appropriate laser power (e.g., over 10 Watts). Selection of a particular laser is generally dependent on the material chosen for the optically opaque layer. In one example, the laser may comprise a relatively low power (e.g., less than or equal to about 30 W) when the optically opaque layer comprises a relatively thin sheet of plastic. In another example, the laser may comprise a relatively high power (e.g., greater than or equal to about 120 W) when the optically opaque layer comprises a relatively thin sheet of metal or a relatively thin layer of metal formed upon an optically transmissive substrate.

According to yet another embodiment, a method is provided herein for inspecting a specimen arranged within an inspection system. In some cases, the method may begin by illuminating an area of the specimen. In some embodiments, the illuminated area may include a two-dimensional field of view (FOV) on the specimen. In such embodiments, the method may utilize a flood illuminated based inspection system for inspecting the specimen. However, the method is not limited to flood illumination based inspection systems in all embodiments of the invention, and may include other types of inspection systems.

In some embodiments, the method may inspect the specimen for defects by using a predetermined mask to filter light reflected and diffracted from periodic structures on the specimen. For example, a predetermined mask may be used when a pattern of light reflected and diffracted from the periodic structures (i.e., a diffraction pattern) is known prior to the step of illuminating. In some embodiments, the predetermined mask may include a chrome mask Fourier filter.

In other embodiments, the method may inspect the specimen for defects by using a custom mask to filter light reflected and diffracted from periodic structures on the specimen. For example, a custom mask may be fabricated "on the fly" (i.e., during the inspection process) to block light reflected and diffracted from the periodic structures on the specimen and to allow light scattered from defects on the specimen to pass through. The method may choose to fabricate the custom mask if the diffraction pattern is unknown prior to the step of illuminating and a predetermined mask is unavailable or otherwise unsuitable for the inspection process. The custom mask may comprise any of the Fourier filter embodiments described herein and may be fabricated in accordance with any of the fabrication processes described herein. As such, the custom mask may be fabricated relatively quickly (e.g., within minutes) and with relatively little cost.

In general, the custom mask may be fabricated by generating an image of light in a Fourier plane of the inspection system, where the image comprises light reflected and diffracted from the structures on the specimen. The generated image (i.e., an image of the diffraction pattern) may then be used to fabricate the custom mask. For example, the image may be used to form an array of patterned features within an optically opaque layer, such as a relatively thin sheet of metal, a relatively thin sheet of plastic or a relatively thin layer of metal formed upon an optically transmissive substrate. In some embodiments, the array of patterned features may be formed by removing select portions of the optically opaque layer with laser light. As noted above, the select portions may only allow the light scattered from defects on the specimen to pass through the custom mask. As such, the custom mask formed by the method may enable defects to be detected more easily.

BRIEF DESCRIPTION OF THE DRAWINGS

Other objects and advantages of the invention will become apparent upon reading the following detailed description and upon reference to the accompanying drawings in which.

Figure 1A:
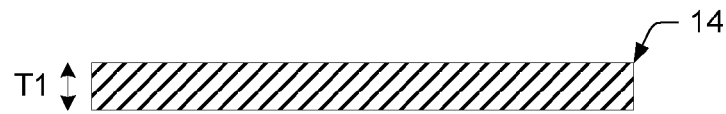
FIG. 1A is a side view illustrating one embodiment of an optically opaque layer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1B:
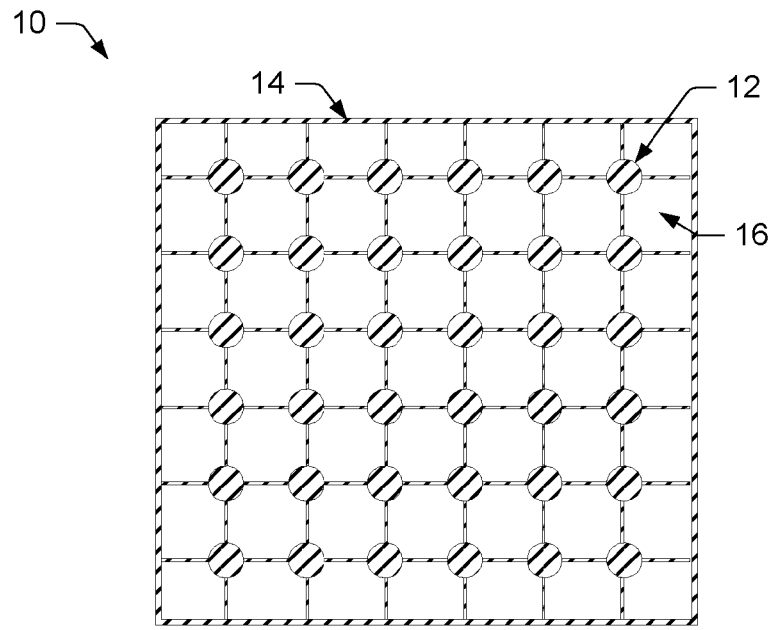
FIG. 1B is a top view illustrating one embodiment of a Fourier filter, in which an array of patterned features is formed within the optically opaque layer of FIG. 1A.
Figure 1C:
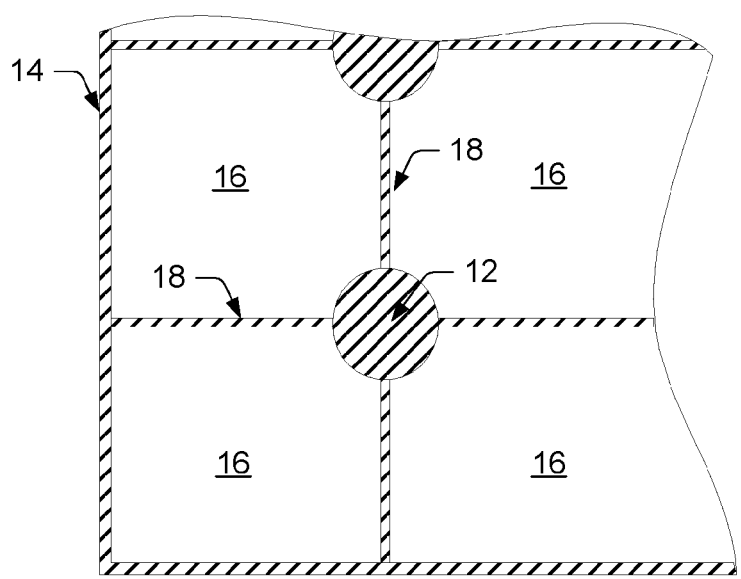
FIG. 1C is a partial, expanded view of one of the patterned features shown in FIG. 1B, including an optically opaque center portion surrounded by a plurality of transmissive regions and suspended there between by a plurality of spider legs.

FIGS. 1A-1C illustrate one embodiment of a Fourier filter 10 configured for use in an inspection system. In the illustrated embodiment, Fourier filter 10 includes an array of patterned features 12 configured to filter light from repetitive structures on a specimen (not shown in FIGS. 1A-1C) illuminated by an inspection system (not shown in FIGS. 1A-1C). As described in more detail below, the array of patterned features 12 is configured to block light reflected and diffracted from periodic structures on the specimen and to allow light scattered from defects on the specimen to pass through the filter to a collection subsystem of the inspection system. The array of patterned features 12 is formed by removing portions of an optically opaque layer 14 to create transmissive regions 16, which only allow the light scattered from defects to pass through. As such, Fourier filter 10 may be used within an inspection system configured for detecting defects based on scattered light. In one embodiment, Fourier filter 10 may be configured for use in a dark field (DF) inspection system.

In some embodiments, Fourier filter 10 may be configured for use in a flood illumination based inspection system. As known in the art, flood illumination based inspection systems illuminate an area of the specimen with a two-dimensional (2D) field of view (FOV), thereby "flood" illuminating the specimen. Such illumination produces diffraction peaks that resemble a 2D array of "dots" in the Fourier plane of the inspection system. In some embodiments, Fourier filter 10 may provide 2D Fourier filtering in a flood illumination based inspection system by including a 2D array of patterned features. However, Fourier filter 10 is not limited to 2D arrays and may alternatively include a one-dimensional (1D) array of patterned features in at least one embodiment of the invention.

Although the array of patterned features 12 shown in FIG. 1B includes a particular number of patterned features, it is to be understood that the Fourier filter embodiments described herein may include any suitable number of patterned features positioned in any suitable arrangement. In addition, although the patterned features 12 shown in FIG. 1B have a generally circular shape, it is to be understood that the shape and dimensions of the patterned features may be selected as described further herein. In particular, characteristics of the patterned features (e.g., the number, position, arrangement, shape, etc.) may be selected based on a diffraction pattern generated at the Fourier plane of the inspection system in response to light reflected and diffracted from structures on the specimen.

Figure 2A:
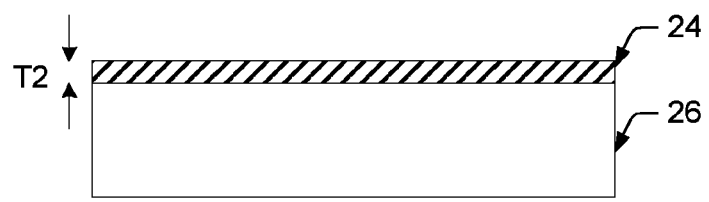
FIG. 2A is a side view illustrating one embodiment of an optically opaque layer formed upon and in contact with an optically transmissive substrate.
Figure 2B:
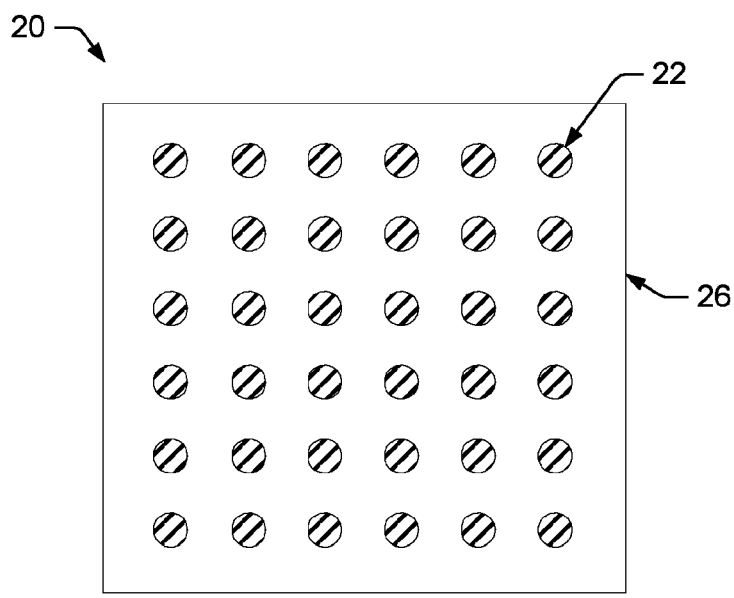
FIG. 2B is a top view illustrating another embodiment of a Fourier filter, in which an array of patterned features is formed within the optically opaque layer of FIG. 2A.
Figure 2C:
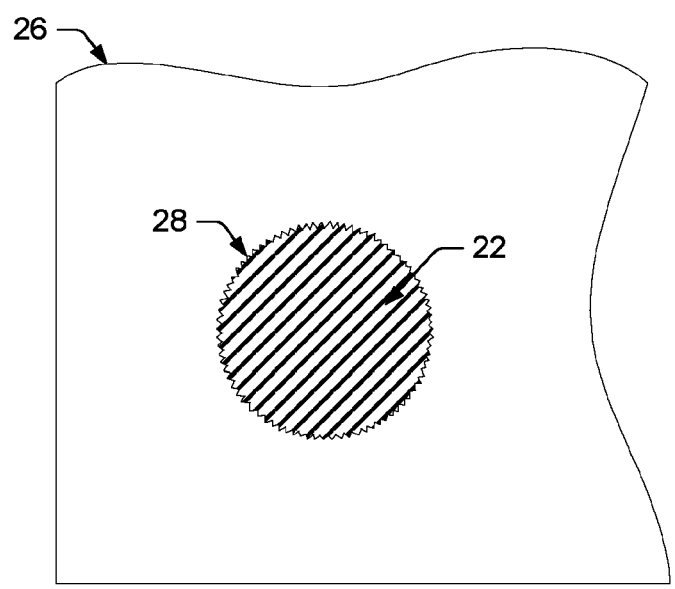
FIG. 2C is a partial, expanded view of one of the patterned features shown in FIG. 2B, including an optically opaque center portion surrounded a transmissive region.

As noted above, the array of patterned features 12 may be formed by removing select portions of an optically opaque layer 14 to create transmissive regions 16, which only allow light scattered from defects on the specimen to pass through the filter. The manner in which the select portions are removed is somewhat dependent on the material chosen for optically opaque layer 14. In some embodiments, the select portions may be cut out of the optically opaque layer 14 when a relatively thin sheet of metal or plastic is used. In other embodiments, the select portions of the optically opaque layer may be evaporated when the layer is coated, or otherwise formed upon, an optically transmissive substrate, as shown in FIGS. 2A-2C.

In the embodiment of FIGS. 1A-1C, optically opaque layer 14 includes a relatively thin sheet of metal or plastic. Examples of suitable metals include stainless steel and other metals (such as aluminum and nickel) with structural integrity. In one embodiment, a sheet of stainless steel having a thickness (T1) of approximately 80 μm may be used to fabricate Fourier filter 10. Examples of suitable plastics include polycarbonate substrates, acrylic substrates, PEEK substrates and other substrates, which are relatively hard and demonstrate relatively little deformation at high temperatures. In one embodiment, a polycarbonate substrate having a thickness (T1) of about 80 μm or more may be used to fabricate Fourier filter 10. However, the thickness (T1) of optically opaque layer 14 typically varies, depending on the particular material chosen for optically opaque layer 14 and the desired mechanical stability of the filter.

In some embodiments, a laser may be used to cut out the select portions of optically opaque layer 14. In order to maintain mechanical stability, the laser may be programmed to create multiple transmissive regions 16 surrounding each of the patterned features 12. For example, an image of the diffraction pattern generated at the Fourier plane of the inspection system may be captured and downloaded to the laser, as described below in reference to FIGS. 4-5. The image may then be used by the laser to remove select portions of the optically opaque layer with relatively high precision and accuracy. Alternative means for removing the select portions may be used in other embodiments of the invention. In one example, a water jet (or other means for cutting) may be used to fabricate Fourier filter 10. However, incorporating a wet process into the fabrication facility may present some difficulties, and thus, may not be desired in all embodiments.

In some embodiments, the laser (or water jet) may be programmed to create four transmissive regions 16 around each of the pattern features 12, as illustrated in FIGS. 1B and 1C. The patterned features (referred to herein as "optically opaque center portions") may be suspended between the transmissive regions by relatively thin strips 18 (referred to herein as "spider legs") of the optically opaque material 14. Four spider legs 18 are used in the current embodiment for suspending the optically opaque center portions 12 within the transmissive regions 16. However, the Fourier filter embodiments described herein are not limited to the particular number or arrangement of transmissive regions and spider legs shown in FIGS. 1B and 1C. In some embodiments, a greater or lesser number of transmissive regions and spider legs may be used, depending on the material chosen for optically opaque layer 14.

In some embodiments, the width of spider legs 18 may be minimal (e.g., less than about 50 μm) when optically opaque layer 14 comprises a metal, such as stainless steel. In some embodiments, the width of spider legs 18 may be somewhat larger (e.g., about 100 μm) when optically opaque layer 14 comprises a plastic, such as a polycarbonate substrate. However, the width of the spider legs created in either embodiment will be substantially smaller than the width of the mechanical rods (e.g., about 1.3 mm) currently used in many Fourier filter designs. Therefore, the embodiments of Fourier filters described herein may be used to increase defect sensitivity over conventional systems, which utilize the mechanical method.

In some embodiments, the optically opaque center portions 12 may have rough edges. For example, although the average shape of the center portions 12 may be generally circular, the edge of the center portions may have a relatively irregular shape, which causes the edges to be relatively rough. The rough edges reduce ringing in the output signal generated by the inspection system by smoothing the transition between blocking and transmitting regions of the Fourier filter. In some embodiments, the rough edges may be produced when the select portions are cut out of the optically opaque layer 14 to create center portions 12 and transmissive regions 16. For example, a laser (or water jet) may be programmed to cut "grooves" or other irregularities within the periphery of the optically opaque center portions 12.

Several factors may be considered when choosing a particular material for optically opaque layer 14. In some embodiments, a relatively thin sheet of metal may be chosen over a plastic substrate when outgassing and photocontamination are not corrected for in the fabrication process. In other words, most plastic materials experience some degree of "outgassing" when exposed to DUV light (such as the DUV light used in dark field inspection systems). However, steps can be taken to prevent the gasses from contaminating optics in the optical path of the inspection system. For instance, a small sputtering system can be used to coat the plastic substrate 14 with a metallic material (e.g., aluminum, gold and other metals commonly used in SEM work; not shown), thereby preventing outgassing and photocontamination from a plastic substrate Fourier filter. On the other hand, a local purge pocket may be created for the filter, so that outgas will contaminate optics outside of the optical path of the inspection system. Although a relatively thin sheet of metal may be chosen over plastic in some embodiments, it may not be preferred in all embodiments of the invention, due to the disadvantages described below.

In some embodiments, a plastic substrate may be chosen over a thin sheet of metal to reduce cost and area consumed in the fabrication facility. For example, a relatively high power laser (e.g., a 120 W $CO_2$ laser or greater) is typically needed to cut the metal layer. Because such lasers are expensive and have relatively large footprints, they may not be practical in all fabrication facilities. On the other hand, plastic substrates may be cut with relatively low power lasers (e.g., a 20 W $CO_2$ laser), which are significantly smaller and less expensive. In one example, a "tabletop" laser cutter such as the VersaLaser VL-200™ may be incorporated within the inspection system for fabricating the Fourier filter embodiments described herein. Such tabletop models are generally available for less than about $12,000 and enable plastic substrate Fourier filters to be produced within a matter of minutes. For this reason, optically opaque layer 14 may include a plastic substrate in at least one preferred embodiment of the invention.

However, the Fourier filter described herein is not limited to a thin sheet of metal or plastic in all embodiments of the invention. In some embodiments, a Fourier filter 20 may include a relatively thin layer of metal 24, which is coated or otherwise formed upon an optically transmissive substrate 26, as shown in FIGS. 2A-2C. Examples of suitable optically transmissive substrates 26 include fused silica, calcium fluoride ($CaF_2$) and magnesium fluoride ($MgF_2$) substrates. However, optically transmissive substrate 26 is not limited to the materials specifically mentioned herein, and may include other substrate materials capable of passing UV light.

Examples of suitable metal materials 24 include aluminum, chromium, gold and other UV blocking films. Metal layer 24 may be formed upon substrate 26 using substantially any means known in the art (including, e.g., sputtering and deposition techniques). In one embodiment, a plasma assisted sputtering technique may be used to form metal layer 24 upon optically transmissive substrate 26. The thickness (T2) of the metal layer generally varies, depending on the particular material chosen for metal layer 24. Regardless of the particular metal layer chosen, substrate 26 is typically coated with an antireflection (AR) coating before the thin layer of metal 24 is formed thereon to reduce back reflection, optical flare and ghosting. In some cases, the AR coating may be a couple nanometers (nm) thick.

In some embodiments, a laser may be used to form the array of patterned features 22 shown in FIGS. 2B and 2C. For example, an image of the diffraction pattern generated at the Fourier plane of the inspection system may be captured and downloaded to the laser, as described below in reference to FIGS. 4-5. The image may be used by the laser to evaporate select portions of metal layer 24, leaving the optically transmissive substrate in tact with the array of patterned features 22 formed thereon. In some cases, the laser power may need to be moderately high (e.g., over 30 W) to evaporate the thin UV blocking films 24. In some cases, the surface of the exposed substrate 26 may not be clean after the evaporation procedure. In these cases, an additional cleaning step may be incorporated within the filter fabrication process to clean the surface of the exposed substrate. In one example, the surface may be cleaned with clean dry air.

In some embodiments, the patterned features 22 may have rough edges 28 as shown, for example, in FIG. 2C. The rough edges may be produced when the select portions are evaporated from metal layer 24 to create the patterned features or "optically opaque center portions" 22. For example, a laser may be programmed to cut "grooves" or other irregularities within the periphery of the optically opaque center portions 22. As noted above, the rough edges may reduce ringing in the output signal generated by the inspection system by smoothing the transition between blocking and transmitting regions of the Fourier filter 20.

In some embodiments, Fourier filter 20 may be preferred over Fourier filter 10. For example, Fourier filter 20 does not need "spider legs" to hold the patterned features in place. Fourier filter 20, therefore, allows larger amounts of scattered light to pass through the filter and does not suffer the additional ringing produced by the spider legs used in Fourier filter 10. However, Fourier filter 20 requires high quality optical substrates with AR coatings, which considerably increase material costs compared to Fourier filter 10. Therefore, Fourier filters 10 and 20 represent a trade-off between defect sensitivity and cost.

In some embodiments, the Fourier filters described herein can be used for spatial Fourier filtering in flood illuminated DF inspection systems. Fourier filtering is commonly used in DF inspections systems to filter out repetitive patterns. Defect signals in the array areas are significantly enhanced by Fourier filtering. However, during use, the Fourier filter will be positioned in the high resolution imaging path of the DF inspection system. Such systems commonly have a relatively high numerical aperture (e.g., an NA of about 0.5 to about 0.99) and relatively short wavelengths (e.g., less than about 300 nm). Therefore, the Fourier filter must meet relatively stringent surface error requirements, including a surface roughness of less than about 4 nm, a wave higher order surface error of less than about $1/40$ (e.g., for $3^{rd}$ orders and higher), and rough filter patterns to reduce ringing in the final image. The Fourier filter embodiments shown in FIGS. 1 and 2 meet the surface error requirements for DF inspection systems.

The Fourier filter embodiments described herein provide a number of advantages over other Fourier filters. For example, the Fourier filter embodiments described herein have relatively high optical quality, relatively small distortion, and relatively small ringing. In some embodiments, a Fourier filter may be formed on a relatively high quality DUV transmitting substrate, such as fused silica. As such, the Fourier filter may not have any pixilated artifices. Furthermore, as described further herein, a laser may be used in preferred embodiments of the invention to form the Fourier filter with relatively high accuracy and precision. In some cases, the laser may further be used to roughen the edges of the patterned features, thereby minimizing the amount of ringing produced by the filter. Moreover, the Fourier filter embodiments described herein may be fabricated with relatively fast turn around time (e.g., usually within minutes) and with relatively low cost of ownership (e.g., the cost of the laser used to form the filter).

Figure 3:
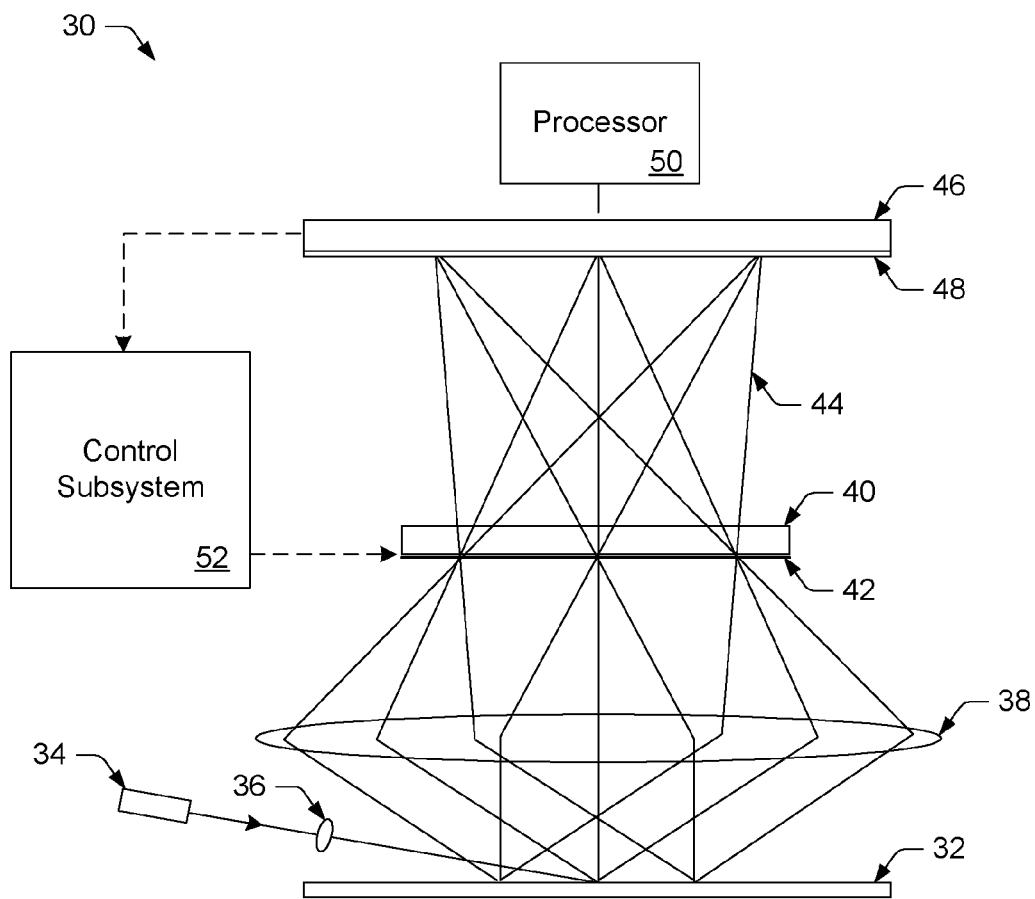
FIG. 3 is a schematic diagram illustrating one embodiment of a system configured to inspect a specimen.

FIG. 3 illustrates one embodiment of a system configured to inspect a specimen. The system 30 includes an illumination subsystem configured to illuminate a specimen 32. The illumination subsystem includes light source 34. Although light source 34 may comprise any suitable light source known in the art, a laser light source is typically used to illuminate the specimen. As such, system 30 may be configured for narrow band (NB) illumination and inspection. The light generated by light source 34 may have any suitable wavelength or wavelengths known in the art, such as visible, UV, DUV, near vacuum ultraviolet (near-VUV), VUV, or some combination thereof. In some embodiments, the light source may be configured to generate light having wavelength(s) of less than about 300 nm. The wavelength(s) of light generated by light source 34 may be selected based on, for example, one or more characteristics of the specimen, one or more characteristics of the defects of interest, and one or more characteristics of the optical components of the system. In addition, the light source may be configured to generate coherent light or incoherent light.

The illumination subsystem may also include objective 36. Objective 36 may be configured to focus light generated by light source 34 onto specimen 32. In some cases, objective 36 may be configured to direct light to the specimen at an oblique angle of incidence, as shown in FIG. 3. The oblique angle of incidence may include any suitable oblique angle of incidence known in the art. In some cases, objective 36 may include one refractive optical element, as shown in FIG. 3. However, objective 36 may alternatively include one or more refractive and/or reflective optical elements not specifically shown herein. In other words, objective 36 may include any suitable optical element(s) known in the art. Examples of suitable optical element(s) include, but are not limited to, spectral filters, polarizing components, beam shaping elements, apertures and any other optical elements known in the art.

The illumination subsystem described above is also configured to illuminate a 2D FOV on the specimen. For example, the illumination subsystem may be configured to illuminate an area on the specimen with an FOV, which includes a relatively large number of pixels in opposing directions (e.g., one hundred or more pixels by one hundred or more pixels). As such, the illumination subsystem may provide a type of illumination commonly referred to as "flood illumination." In contrast to flood illumination, spot illumination used in spot scanning inspection systems commonly illuminates relatively few pixels on the specimen.

System 30 also includes a collection subsystem configured to collect light from specimen 32. In one embodiment, the collection subsystem includes a lens 38 configured to collect light scattered from specimen 32. Lens 38 is also configured to collect light reflected and diffracted from periodic structures (not shown) on specimen 32. The periodic structures may include any periodic structures known in the art. Lens 38 may include an objective lens, a Fourier transform lens, or any other suitable optical element known in the art. Although the collection subsystem shown in FIG. 3 includes only one lens 38, it is to be understood that the collection subsystem may include more than one optical element (e.g., one or more refractive and/or reflective optical elements). Further more, the collection subsystem may include any other suitable optical elements known in the art. In some embodiments, the light collected from the specimen may include DUV when the specimen is illuminated by the illumination subsystem in this range.

The collection subsystem also includes a Fourier filter 40 positioned at a Fourier plane 42 (i.e., an image plane) of the collection subsystem. The Fourier filter may be configured as described above and shown in FIGS. 1 and 2. For example, Fourier filter 40 may include an array of patterned features. The patterned features may be configured to filter light from repetitive structures (not shown) on specimen 32. In particular, the patterned features may be configured to block light reflected and diffracted from periodic structures on the specimen and to allow light scattered from defects on the specimen to pass through the Fourier filter to the collection subsystem. The array of patterned features may be formed as described above. For example, a laser may be used to form the array of patterned features by removing select portions of an optically opaque layer to create transmissive regions, which only allow the light scattered from the defects to pass through.

In some embodiments, Fourier filter 40 may be used to provide 2D Fourier filtering in a flood illumination based DF inspection system 30. For example, the Fourier filter 40 may include 2D array of patterned features for blocking a 2D pattern of light diffracted from periodic structures on the specimen. Characteristics of the patterned features may be selected based on one or more characteristics (e.g., dimensions, pitch, etc.) of the periodic structures on the specimen. For example, the 2D pattern of diffracted light (i.e., the diffraction pattern produced by the periodic structures on the specimen) may be imaged in Fourier plane 42 and collected by the collection subsystem. The image generated at the Fourier plane may be used to select characteristics of Fourier filter 40, which prevent the diffraction pattern from passing through.

Figure 4:
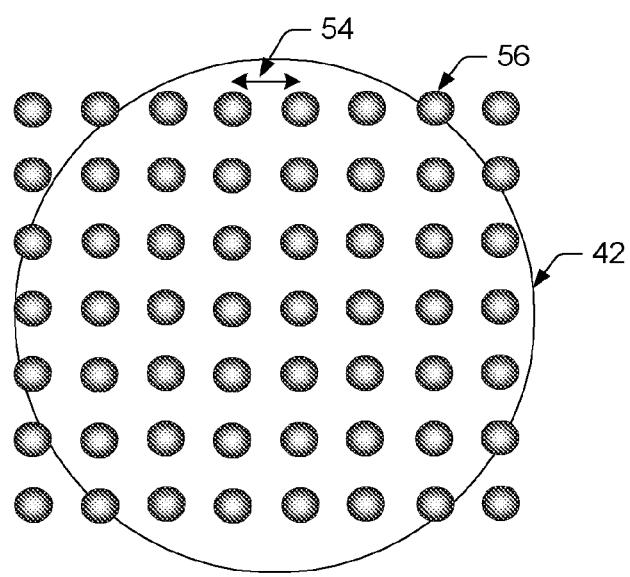
FIG. 4 is a top view illustrating one example of a diffraction pattern that may be observed in a Fourier plane of a flood illumination based inspection system.

FIG. 4 illustrates an exemplary diffraction pattern produced by periodic structures having a 3 µm pitch at the Fourier plane 42 of an inspection system 30 having a numerical aperture (NA) of about 0.7. The $\Delta$NA spacing 54 between diffraction blurs 56 in Fourier plane 42 is $\lambda/\Lambda$=0.266 µm/3 µm=0.089, where $\lambda$ is the wavelength and $\Lambda$ is the pitch. For a system having a relatively high NA (e.g., an NA of about 0.9) and a Fourier plane having dimensions of about 20 mm, the distances between diffraction blurs 56 is about 1.9 mm. In order to completely block the diffraction pattern shown in FIG. 4, each of the patterned features included within the Fourier filter may have an area of about 2.0 mm by about 2.0 mm. However, the patterned features are not limited to such an area in all embodiments of the invention. As described in more detail below, the area of the patterned features may generally range between about 0.1 mm×0.1 mm and about 2.0 mm×2.0 mm.

In some embodiments, the array of patterned features may be configured for blocking a maximum of about 16% of the area within the Fourier plane, while blocking a minimum of about 99% of the light reflected and diffracted from the periodic structures. In other words, good Fourier filtering performance is preferably achieved by blocking substantially all diffraction "blurs," while blocking as little other scattered light as possible. The maximum Fourier plane blur allowed for 16% blockage is about 0.86 mm in diameter. 16% blockage is used in this example merely as a frame of reference since it is the blockage of some currently used Fourier filters. Blockage in excess of 16% tends to reduce the maximum defect signal that can be detected, thereby reducing the defect sensitivity of the inspection system. As such, embodiments of the Fourier filters described herein preferably do not exceed 16% blockage. However, the allowable blur may vary depending on the particular optics used in the inspection system (e.g., diffraction from the optics or point spread function (PSF) of the optics).

In some embodiments, specimen 32 may be illuminated with coherent illumination. For coherent illumination systems, the allowable diffraction blur may be on the order of about 0.15 mm. As such, the patterned features included within the Fourier filter may have a "pixel" size or spot size of less than about 0.15 mm. In one example, the Fourier filter pixel size may be less than about 50 µm with a placement better than about 25 µm. In other words, an array of about 4 pixels by 4 pixels, each pixel having a size of about 50 µm, may block a diffraction order with a diffraction blur of about 0.15 mm. In other embodiments, specimen 32 may be illuminated with incoherent illumination. With incoherent illumination, an array of up to about 22 pixels by about 22 pixels, each having a size of about 50 µm, may block the diffraction order.

The arrangement of the patterned features is preferably selected, so as to block the diffraction pattern with the smallest possible area of patterned features. In addition, the size of the patterned features may be selected based on the diffraction blur in combination with the diffraction of the optics. For example, if the diffraction blur has a size of about 1 mm, the size of the patterned features may be about 1.3 mm to ensure that diffraction caused by the periodic structures on the specimen as well as any diffraction caused by the optics of the inspection system is blocked by the Fourier filter.

Blocking the diffraction pattern with the smallest possible area of patterned features is advantageous for a number of reasons. For example, the Fourier filter embodiments described herein are configured for blocking diffraction peaks in the light reflected and diffracted from periodic structures on the specimen, while allowing a larger amount of scattered light to be detected. In other words, light diffracted from periodic structures tends to be relatively bright in comparison to light scattered from defects on the specimen. By preventing the diffracted light from being detected (e.g., by a detection subsystem described further herein), the Fourier filter embodiments described herein increase the accuracy with which the light scattered from defects can be detected. As such, the Fourier filter embodiments described herein enable a significantly larger amount of scattered light to pass through (compared to mechanical filters and previous implementations of Fourier filters) by blocking only the diffraction peaks of the light from the periodic structures. When incorporated within an inspection system, the Fourier filter embodiments enable the inspection system to detect higher defect signals, and thus, provide the inspection system with higher defect detection sensitivity than other currently available systems.

Returning to FIG. 3, a detection subsystem is also included within inspection system 30 to generate an output signal responsive to light 44 that passes through Fourier filter 40. In the illustrated embodiment, the detection subsystem includes detector 46 positioned at image plane 48 of the system. The detection subsystem may also include an objective (not shown) configured to image light that passes through Fourier filter 40 onto detector 46. The objective may include, for example, any suitable imaging lens(es) or focusing lens(es) known in the art. Detector 46 may be any appropriate detector known in the art, such as a charge coupled device (CCD) or TDI camera. Detector 46 may be configured to generate the output responsive to the light 44 that passes through the filter 40. The detection subsystem may also include any other suitable optical element(s) (not shown) known in the art.

The output generated by the detection subsystem can be used to detect defects (not shown) on the specimen 32. For example, the system may include processor 50. Processor 50 may be coupled to detector 46 of the detection subsystem by a transmission medium (not shown). The transmission medium may include any suitable transmission medium known in the art. The addition, the processor may be coupled to the detector by one or more electronic components (not shown) such as an analog to digital converter. In this manner, processor 50 is configured to receive output from detector 46.

Processor 50 may be configured to use the output for detecting one or more defects on the specimen. The defects may include any defects of interest on the specimen. In addition, processor 50 may be configured to use the output and any method and/or algorithm known in the art to detect the defects on the specimen. Furthermore, processor 50 may be configured to perform any other inspection-related functions known in the art (e.g., defect location determination, defect classification, defect mapping, etc.). Processor 50 may take various forms, including a personal computer system, mainframe computer system, workstation, image computer, parallel processor, or any other processing device known in the art. In general, the term "computer system" may be broadly defined to encompass any device having one or more processors, which executes instructions from a memory medium.

In some embodiments, a control subsystem 52 may also be included within the inspection system 30. For example, control subsystem 52 may be configured to align the Fourier filter 40 in the Fourier plane 42 by translating the filter until an intensity measured by the detection subsystem is minimized. In this manner, the control subsystem can align the filter to overlap with the diffraction pattern produced by the periodic structures on specimen 32 until a minimum intensity is imaged on the detector 46.

For example, the control subsystem 52 may be coupled to detector 46. The Fourier filter may be inserted into a holder (not shown) mounted on a stage (not shown) such as an x-y stage. The control subsystem may be coupled to the stage in any suitable manner. In addition, the control subsystem may be configured to alter a position of the Fourier filter 40 by causing a position of the stage to change. For example, the control subsystem may include any suitable mechanical and/or robotic assembly configured to move the stage, and thus, alter the position of the filter in the x and y directions of the Fourier plane. If the system includes a subsystem (not shown) for altering the focus of the system (e.g., to account for variations in the height of the specimen), the control subsystem may also be configured to move the Fourier filter in the z direction (e.g., toward and away from the specimen), such that the Fourier filter may be accurately positioned within the Fourier plane of the collection subsystem.

Inserting the Fourier filter into a holder mounted on an x-y stage may increase the ease of filter alignment and filter selection. In addition, the filter may be positioned in the holder for easy "drop in" and to maintain tolerance for the Fourier filter. Furthermore, the holder may include a cassette configured such that different Fourier filters may be positioned in different slots in the cassette. Such a cassette may have any suitable configuration known in the art. In addition, a Fourier filter in the cassette may be positioned in the optical path of the inspection system by the control subsystem, as described above.

It is noted that FIG. 3 is provided herein to generally illustrate one embodiment of a system configured to inspect a specimen. Obviously, the system configurations described herein may be altered to optimize the performance of the system, as is normally performed when designing a commercial inspection system. In some cases, the systems described herein may be implemented using an existing inspection system (e.g., by inserting an embodiment of a Fourier filter described herein within an existing inspection system, such as one of the Puma 900 Series tools that are commercially available from KLA-Tencor of San Jose, Calif.). For such systems, the inspection functionality described herein may be provided as optional functionality of the system (e.g., in addition to other functionality of the system). In other cases, the systems described herein may de designed "from scratch" to provide a completely new system.

Figure 5A:
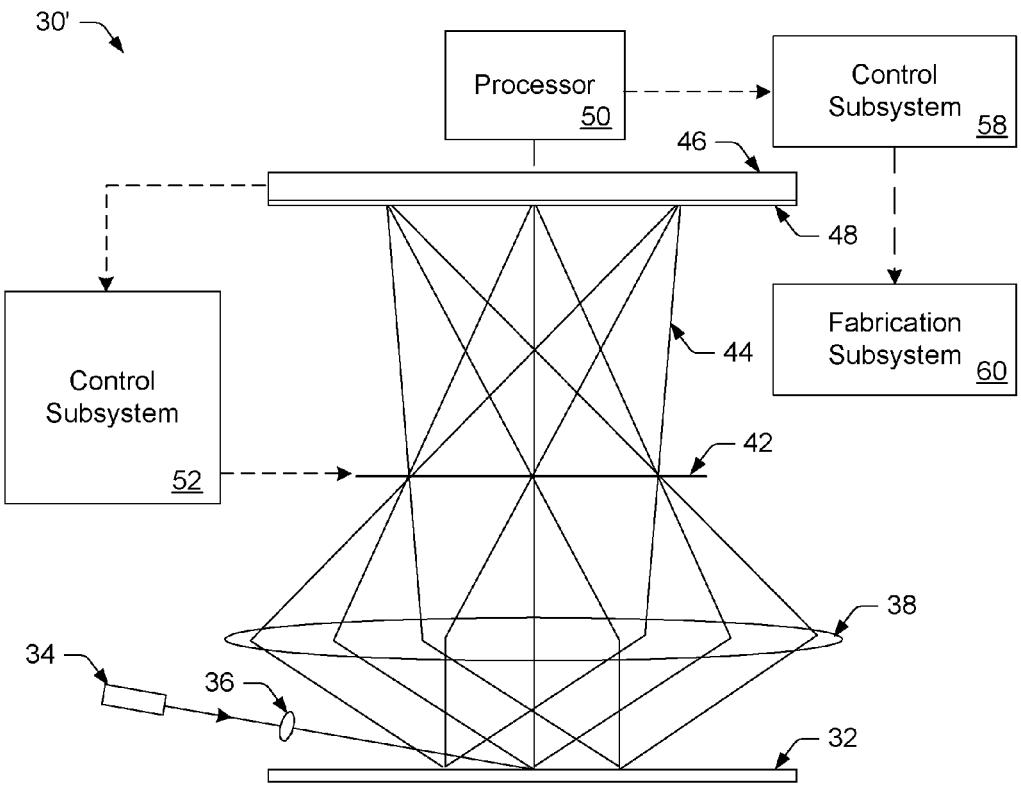
FIG. 5A is a schematic diagram illustrating one embodiment of a system configured to fabricate a Fourier filter for use in an inspection system.
Figure 5B:
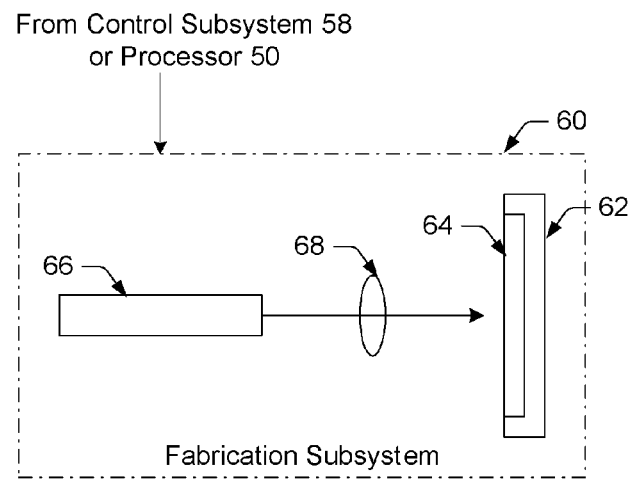
FIG. 5B is a schematic diagram illustrating one embodiment of a fabrication subsystem that may be included within the system of FIG. 5A.

FIGS. 5A-5B illustrate one embodiment of a system 30' configured to fabricate a Fourier filter for use in an inspection system. Many of the components shown in FIG. 5A are included in the inspection system of FIG. 3 and described in detail above. For the sake of brevity, similar components indicated with similar reference numerals will not be described further herein. As described in more detail below, additional components may be added to the inspection system of FIG. 3 to fabricate the Fourier filter.

In general, inspection system 30' includes an optical subsystem, which is configured to generate an image of light in the Fourier plane 42 of the inspection system. The image of light includes light reflected and diffracted from structures on the specimen 32. Unlike the inspection system of FIG. 3, however, the image of light is generated without a Fourier filter positioned at the Fourier plane 42. This enables the inspection system to measure the light reflected and diffracted from periodic structures on the specimen without the blockage provided by the Fourier filter.

The inspection system 30' also includes a detection subsystem configured to capture an image of the light generated at the Fourier plane 42. In some embodiments, the detection subsystem may use the same camera to generate the image of light before and after the filter install. For example, detector 46 may be positioned at image plane 48, as described above in reference to FIG. 3. Detector 46 may include any of the detectors described herein, or any other suitable viewer or camera known in the art. During filter fabrication, detector 46 may be configured to generate an output signal responsive to the image of the light in the Fourier plane of the system, including light reflected and diffracted from periodic structures on the specimen.

In other embodiments, the detection subsystem may use a different camera to generate the image of light before and after the filter install. For example, a beam splitter (or any other suitable optical component known in the art, not shown) may be positioned in the path of the light that passes through Fourier plane 42 when the image of light is being measured for fabrication of a new Fourier filter. During subsequent inspection of a specimen, the beam splitter or other optical component may be removed from the optical path of the inspection system. The beam splitter (or other optical component) may be removed from the optical path of the inspection system in any manner known in the art. For example, the optical component may include a flip-in mount (not shown), the position of which may be controlled by control subsystem 52 and/or processor 50. In another example, the control subsystem may alter a position of the beam splitter similar to the manner in which the position of the Fourier filter is controlled. The light refracted by the beam splitter (or other optical component) may be directed to an additional detector (not shown) for generating the image of light to be used in fabricating the Fourier filter.

Processor 50 may be coupled to receive the image from the detector (i.e., detector 46 or the additional detector, not shown). The processor may be coupled to the detector as described above. In addition, the processor may be coupled to a control subsystem 58 and a fabrication subsystem 60, as shown in FIGS. 5A and 5B. The processor may be coupled to the control subsystem by a transmission medium. The transmission medium may include any suitable transmission medium known in the art.

In one embodiment, fabrication subsystem 60 may include a "laser cutter." The laser cutter may include any appropriate laser source (e.g., a $CO_2$ laser, semiconductor laser, etc.) having any appropriate laser power (e.g., about 20 W to about 200 W). As such, laser cutter 60 may be a relatively high power laser having a relatively large footprint, or a relatively low power laser having a relatively small footprint. In one embodiment, laser cutter 60 may be a "tabletop" laser cutter, such as the VersaLaser VL-200™. Such tabletop models are currently available for less than about $12,000 and enable embodiments of the Fourier filters described herein to be produced within a matter of minutes. However, fabrication subsystem 60 is not limited to a laser cutter in all embodiments of the invention. In some embodiments (not shown), fabrication subsystem 60 may include alternative means (e.g., a water jet) for removing select portions of an optically opaque layer to fabricate the Fourier filter embodiments described herein.

As shown in FIG. 5B, a holder 62 may be included within fabrication subsystem 60 for mounting a "blank" 64 prior to removal of the select portions. For example, optically opaque layer 64 may be mounted within holder 62 prior to exposing the optically opaque layer to light from laser light source 66. As such, optically opaque layer 64 may be referred to as a "blank" before laser light is used to form the pattern of features therein. In some cases, an alignment tolerance may be built into holder 62, so that the size of the blank is not critical.

As noted above, optically opaque layer 64 may include a number of different materials. Examples of suitable materials include, but not limited to, a relatively thin sheet of metal, a relatively thin sheet of plastic or a relatively thin layer of metal formed upon an optically transmissive substrate. As noted above, light source 66 may include any appropriate laser source having any appropriate laser power. Selection of a particular laser source 66 is generally dependent on the material chosen for optically opaque layer 64. As shown in FIG. 5B, the light from light source 66 may be directed to optically opaque layer 64 via one or more optical components 68. Optical components 68 may include any number and/or type of suitable optical or mechanical components known in the art.

As shown in FIG. 5B, fabrication subsystem 60 may be configured to fabricate the Fourier filter embodiments described herein by using laser light to form an array of patterned features within optically opaque layer 64. As shown in FIG. 5A, control subsystem 58 may be included for controlling the filter fabrication based on the image generated by the optical subsystem and detected by the detection subsystem. In one example, an image of the diffraction pattern generated at Fourier plane 42 may be downloaded from processor 50 to control subsystem 58. In another example (not shown), control subsystem 58 may be directly coupled to detector 46 (or to an additional detector) for receiving the image generated at the Fourier plane and detected by the detector.

Regardless, control subsystem 58 is configured for controlling one or more of the fabrication subsystem components, such that an array of patterned features is formed within optically opaque layer 64 for blocking the light reflected and diffracted from the periodic structures on the specimen. For example, one or more of the components within fabrication subsystem 60 (e.g., laser source 66, optical component 68 and holder 62) may be mounted on a stage (not shown) for translating the component(s) in appropriate directions. The control subsystem 58 may, therefore, control movement of the stage (s) to direct the laser light to the optically opaque layer 64 in the appropriate manner.

Control subsystem 58 may be configured to control fabrication subsystem 60 in any suitable manner. For example, the control subsystem may be configured to generate a write file or a recipe for forming the patterned features within the optically opaque layer. The write file may be created by using the diffraction pattern in the image generated by the optical subsystem, as well as pattern recognition to identify the diffraction pattern and diffraction orders in the image. The control subsystem may then determine the position and other characteristics (e.g., size, shape, etc.) of the patterned features to be formed within the optically opaque layer by the fabrication subsystem based on the diffraction pattern and diffraction orders (possibly in combination with other information described herein). The control subsystem may use the write file or recipe to control the fabrication subsystem or may provide the write file or the recipe to the fabrication subsystem, so that the fabrication subsystem may form the patterned features within the optically opaque layer.

In some embodiments, control subsystem 58 may control fabrication subsystem 60, such that the patterned features are formed with rough edges. The rough edges of the patterned features may be configured as described herein and may be formed as described further herein. The roughness of the edges may be determined using any suitable algorithm and/or method known in the art. In one embodiment, an algorithm for rough edges may be included in the write files or recipes for fabrication of the Fourier filter to reduce the ringing effect, as further described herein.

Although the system shown in FIGS. 5A and 5B includes control subsystem 52 for positioning the Fourier filter in the Fourier plane and control subsystem 58 for controlling the fabrication subsystem, it is to be understood that the system may instead include a single control subsystem configured to perform both functions. In addition, although illustrated as separate components in FIGS. 5A and 5B, control subsystem 58 may be included within fabrication subsystem 60 in other embodiments of the invention. Furthermore, the control subsystems shown herein may control other aspects of the fabrication process not specifically mentioned herein.

After fabrication, the newly formed Fourier filter may be cleaned and/or sputtered a coating (e.g., a metallic coating may be sputtered onto a plastic substrate Fourier filter to prevent outgassing and photocontamination, as described above). In some cases, the filter may be "dropped into" a system configured for inspecting a specimen. The system may be similar to the inspection system 30 described above in reference to FIG. 3. In other cases, the filter may be placed within a cassette or autoloader coupled to the inspection system. Such a case may be desirable when many different types of specimen are to be inspected by the same system. In some embodiments, filter performance may be verified by obtaining images of the light reflected and diffracted from the periodic structures on the specimen before and after filter install. As but one advantage, the Fourier filter embodiments described herein provide more than 99% blockage of the diffraction pattern produced by the periodic structures. Other advantages may become apparent in light of the discussion provided herein.

Figure 6:
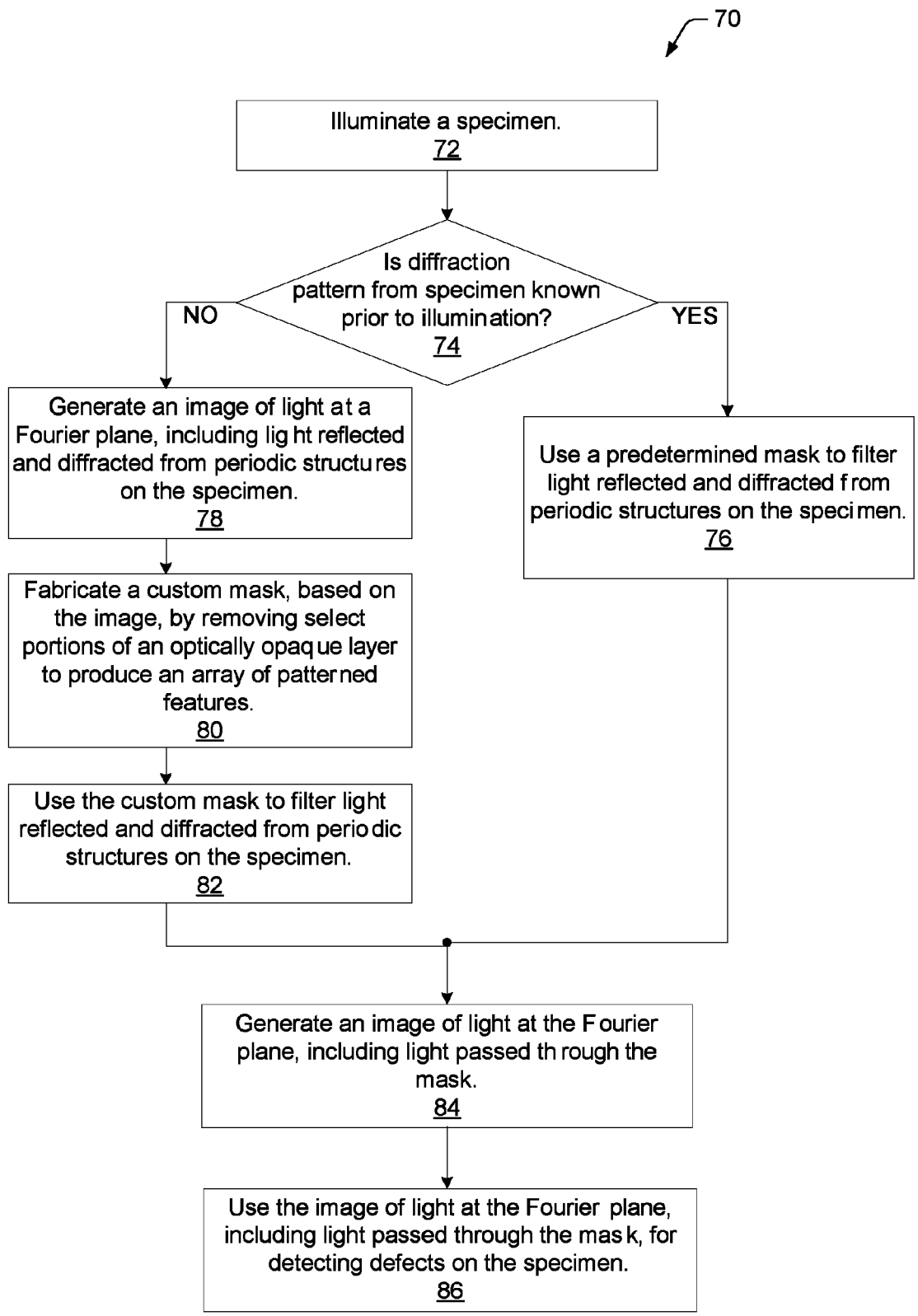
FIG. 6 is a flowchart diagram illustrating one embodiment of a method for inspecting a specimen.

FIG. 6 illustrates one embodiment of a method 70 that may be used for inspecting a specimen arranged within an inspection system. In particular, FIG. 6 provides an embodiment of a method, in which various types of Fourier filters are available for use in the inspection system. As noted above, the Fourier filter embodiments described herein provide many advantages over other types of Fourier filters. Among other advantages mentioned above, the embodiments described herein may be fabricated very quickly (e.g., within minutes) for very little cost (e.g., the additional cost of a laser cutter). As such, the Fourier filter embodiments described herein are well suited for process development and other situations in which quick feedback is needed or desired. However, the Fourier filter embodiments described herein may not be preferred at all times.

In some cases, for example, a chrome mask Fourier filter may be preferred when the diffraction patterns generated by the periodic structures on the specimen are well known (as may occur, e.g., during production line monitoring). As noted above, chrome masks provide good repeatability and matching to semiconductor wafers, since they are fabricated with the same processes (e.g., lithography and etch). However, chrome masks are generally unsuitable for process development, due to the long turn around time and cost associated with fabricating such masks. The method shown in FIG. 6 provides the option of using a predetermined mask (such as a chrome mask or other Fourier filter) or fabricating a custom mask (such as any of the Fourier filter embodiments described herein) to filter the light reflected and diffracted from periodic structures on the specimen. Therefore, the method shown in FIG. 6 represents an improvement over conventional methods that do not provide the option choosing between a predetermined or custom fabricated mask during the inspection process.

In some embodiments, the method 70 may begin by illuminating an area of the specimen (in step 72). As noted above, the Fourier filter embodiments described herein may be particularly useful in flood illumination based inspection systems. If used in such a system, the illuminated area may include a two-dimensional field of view (FOV) on the specimen. However, the Fourier filter embodiments described herein are not limited to a flood illumination based inspection system in all embodiments of the invention, and may alternatively include a one-dimensional FOV.

Next, the method may determine if a pattern of light reflected and diffracted from periodic structures on the specimen is known prior to the step of illuminating (in step 74). If the diffraction pattern is known, the method may inspect the specimen for defects using a predetermined mask (in step 76). In particular, the predetermined mask may be used to filter the light reflected and diffracted from the periodic structures on the specimen, so that light scattered from defects on the specimen can be detected more easily.

In one embodiment, the predetermined mask may be a chrome Fourier filter mask, which was previously fabricated by depositing chrome on a substrate, patterning the chrome by lithography and etch, and cleaning the substrate with the patterned chrome features formed thereon. Chrome masks usually provide good repeatability and matching to semiconductor wafers fabricated with similar processes (e.g., lithography and etch processes). As such, a chrome mask filter may sometimes be preferred over the Fourier filter embodiments described herein when the diffraction pattern produced by the periodic structures is well known (e.g., during production line monitoring) and a chrome mask filter is readily available. It is noted, however, that the predetermined mask is not limited to a chrome mask Fourier filter in all embodiments of the invention. Other types of pre-fabricated Fourier filters may be used, as desired.

If the diffraction pattern is unknown prior to the step of illuminating, the method may inspect the specimen for defects using a custom mask (in step 82). Like the predetermined mask, the custom mask may be used to filter light reflected and diffracted from the periodic structures on the specimen, so that light scattered from defects on the specimen can be detected more easily. Unlike the predetermined mask, however, the custom mask may be fabricated "on the fly" (in steps 78 and 80). As such, the custom mask may be preferred over a predetermined mask when the diffraction pattern produced by the periodic structures is unknown prior to the step of illuminating (e.g., during process development) and when quick feedback about the specimen is needed or desired.

In general, the custom mask may comprise any of the Fourier filter embodiments described herein. The custom mask may also be fabricated by any means described herein. For example, an image of light reflected and diffracted from periodic structures on the specimen may be generated at a Fourier plane of an inspection system (in step 78). The image of light may then be used to fabricate the custom mask (in step 80) as further described herein.

In one embodiment, the image of light may be supplied to a fabrication subsystem, such as the one illustrated in FIGS. 5A and 5B. In general, the custom mask may be fabricated by removing select portions of an optically opaque layer to produce an array of patterned features. In some embodiments, the select portions may be removed by using laser light to cut or evaporate the select portions out of the optically opaque layer, as further described herein. In other embodiments, the select portions may be removed by alternative means (e.g., a water jet). Regardless of the particular means used to form the array of patterned features, the array may be configured to block light reflected and diffracted from structures on the specimen and to allow light scattered from defects on the specimen to pass through. As noted above, the array may provide more than about 99% blockage of the light reflected and diffracted from the structures on the specimen, thereby enabling light scattered from defects on the specimen to be detected with greater accuracy.

It will be appreciated to those skilled in the art having the benefit of this disclosure that this invention is believed to provide Fourier filters, inspection systems and systems and methods for fabricating Fourier filters. More specifically, the invention provides an improved Fourier filter, which can be designed and fabricated in a matter of minutes, while maintaining good filtering characteristics. Further modifications and alternative embodiments of various aspects of the invention will be apparent to those skilled in the art in view of this description. It is intended, therefore, that the following claims be interpreted to embrace all such modifications and changes and, accordingly, the specification and drawings are to be regarded in an illustrative rather than a restrictive sense.

What is claimed is:

1. A method for fabricating a Fourier filter, wherein the method comprises:

generating an image of light in a Fourier plane of an inspection system, wherein the image comprises light reflected and diffracted from structures on a specimen being inspected by the inspection system; and fabricating a Fourier filter based on the generated image, wherein the step of fabricating comprises forming an array of patterned features within an optically opaque layer, wherein the array of patterned features is configured to block the light reflected and diffracted from the structures on the specimen and to allow light scattered from defects on the specimen to pass through the filter, and wherein the array of patterned features is formed by removing portions of the optically opaque layer with laser light to create transmissive regions, which only allow the light scattered from the defects to pass through.

2. The method recited in claim 1, wherein the step of fabricating comprises forming a two-dimensional array of the patterned features.

3. The method recited in claim 1, wherein the step of fabricating comprises forming each of the patterned features in the array so as to include an optically opaque center portion surrounded by at least one transmissive region.

4. The method recited in claim 3, wherein a shape of the optically opaque center portion is substantially circular.

5. The method recited in claim 3, wherein a shape of the optically opaque center portion is based on the image of the reflected and diffracted light obtained in the Fourier plane of the inspection system.

6. The method recited in claim 3, wherein the optically opaque layer comprises a relatively thin layer of metal formed upon an optically transmissive substrate.

7. The method recited in claim 6, wherein the optically transmissive substrate comprises a material selected from a group comprising fused silica, calcium fluoride and magnesium fluoride.

8. The method recited in claim 6, wherein the relatively thin layer of metal comprises a material selected from a group comprising chromium, gold, aluminum and other metals capable of blocking deep ultra-violet (DUV) light.

9. The method recited in claim 6, wherein the step of fabricating comprises using the laser light to create the at least one transmissive region by evaporating portions of the relatively thin layer of metal, while leaving the optically transmissive substrate in tact.

10. The method recited in claim 3, wherein the optically opaque center portion is surrounded by two or more transmissive regions and suspended there between by two or more thin strips of the optically opaque layer.

11. The method recited in claim 10, wherein the step of fabricating comprises using the laser light to create the two or more transmissive regions by cutting out portions of the optically opaque layer, leaving the optically opaque center portion and thin strips in tact.

12. The method recited in claim 10, wherein the thin strips comprise a width on the order of tens of microns.

13. The method recited in claim 10, wherein the optically opaque layer comprises a relatively thin sheet of metal.

14. The method recited in claim 13, wherein the relatively thin sheet of metal is selected from a group comprising stainless steel, aluminum and nickel.

15. The method recited in claim 10, wherein the optically opaque layer comprises a relatively thin sheet of plastic.

16. The method recited in claim 15, wherein the relatively thin sheet of plastic is selected from a group comprising polycarbonate, acrylic and PEEK substrates.

17. The method recited in claim 16, wherein the relatively thin sheet of plastic is coated with a metallic material to prevent the plastic from outgassing when exposed to ultra-violet (UV) light.

18. An inspection system, comprising:

an optical subsystem configured to generate an image of light in a Fourier plane of the inspection system, wherein the image comprises light reflected and diffracted from structures on a specimen being inspected by the inspection system;

a fabrication subsystem configured to fabricate a Fourier filter customized for the specimen by using laser light to form an array of patterned features within an optically opaque layer; and a first control subsystem configured to control the fabrication subsystem based on the image generated by the optical subsystem, such that substantially all of the light reflected and diffracted from the structures on the specimen is blocked by the array of patterned features, while light scattered from defects on the specimen is allowed to pass through the Fourier filter.

19. The system as recited in claim 18, wherein the fabrication subsystem comprises:

a holder configured for aligning the optically opaque layer within the fabrication subsystem; and a laser configured to form the array of patterned features by removing select portions of the optically opaque layer under control of the first control subsystem, wherein the select portions removed by the laser only allow the light scattered from the defects on the specimen to pass through the Fourier filter.

20. The system as recited in claim 19, wherein the optically opaque layer comprises a relatively thin sheet of plastic.

21. The system as recited in claim 20, wherein the laser comprises a relatively low power of less than or equal to about 30 W.

22. The system as recited in claim 19, wherein the optically opaque layer is selected from a group comprising a relatively thin sheet of metal, and a relatively thin layer of metal formed upon an optically transmissive substrate.

23. The system as recited in claim 22, wherein the laser comprises a relatively high power greater than about 30 W and less than about 200 W.

24. The system as recited in claim 18, wherein the array of patterned features comprises a two-dimensional array of the patterned features, and wherein each of the patterned features in the two-dimensional array comprises an optically opaque center portion surrounded by at least one transmissive region.

25. The system as recited in claim 18, wherein the optical subsystem comprises:

an illumination subsystem configured to illuminate a two-dimensional field of view on the specimen; and a collection subsystem configured to collect light from the specimen.

26. The system as recited in claim 25, further comprising:

a second control subsystem configured to position the Fourier filter within the Fourier plane of the collection subsystem; and a detection subsystem configured to receive light, which is scattered from defects on the specimen and passed through the Fourier filter, and to generate output responsive to the received light, wherein the generated output can be used to detect the defects on the specimen.

27. The system as recited in claim 25, wherein the system comprises a flood illuminated dark field inspection system.

28. A method for inspecting a specimen arranged within an inspection system, the method comprising:

illuminating an area of the specimen, wherein the illuminated area comprises a two-dimensional field of view on the specimen;

fabricating a custom mask configured to block light reflected and diffracted from structures on the specimen and to allow light scattered from defects on the specimen to pass through, if a pattern of the reflected and diffracted light is unknown prior to the step of illuminating; and inspecting the specimen for defects, wherein the step of inspecting comprises filtering light from the specimen using: (a) the custom mask if the pattern of the reflected and diffracted light is unknown prior to the step of illuminating, or (b) a predetermined mask if the pattern of the reflected and diffracted light is known prior to the step of illuminating.

29. The method as recited in claim 28, wherein the step of fabricating comprises:

generating an image of light in a Fourier plane of the inspection system, wherein the image comprises the light reflected and diffracted from the structures on the specimen; and fabricating the custom mask based on the generated image, wherein the custom mask comprises a Fourier filter having an array of patterned features formed within an optically opaque layer, wherein the custom mask is fabricated by removing select portions of the optically opaque layer with laser light, and wherein the select portions only allow the light scattered from the defects on the specimen to pass through the Fourier filter.

30. The method as recited in claim 28, wherein the predetermined mask comprises a chrome mask Fourier filter.

* * * * *